(12) United States Patent
Chauvier et al.

(10) Patent No.: US 10,273,250 B2
(45) Date of Patent: Apr. 30, 2019

(54) USE FOR BORON FORMATES FOR REDUCING UNSATURATED ORGANIC FUNCTIONS

(71) Applicant: Commissariat a l'Energie Atomique et aux Energies Alternatives, Paris (FR)

(72) Inventors: Clément Chauvier, Paris (FR); Thibault Cantat, Issy les Moulineaux (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/774,844

(22) PCT Filed: Nov. 8, 2016

(86) PCT No.: PCT/EP2016/077007
§ 371 (c)(1),
(2) Date: May 9, 2018

(87) PCT Pub. No.: WO2017/081022
PCT Pub. Date: May 18, 2017

(65) Prior Publication Data
US 2018/0327429 A1 Nov. 15, 2018

(30) Foreign Application Priority Data
Nov. 10, 2015 (FR) ...................................... 15 60752

(51) Int. Cl.
| | | |
|---|---|---|
| *C07C 45/41* | (2006.01) | |
| *C07C 29/00* | (2006.01) | |
| *C07F 5/00* | (2006.01) | |
| *C07F 5/02* | (2006.01) | |
| *C07C 29/14* | (2006.01) | |
| *C07C 29/147* | (2006.01) | |
| *C07C 209/50* | (2006.01) | |
| *C07C 209/52* | (2006.01) | |
| *C07B 31/00* | (2006.01) | |

(52) U.S. Cl.
CPC .............. *C07F 5/025* (2013.01); *C07B 31/00* (2013.01); *C07C 29/14* (2013.01); *C07C 29/147* (2013.01); *C07C 45/41* (2013.01); *C07C 209/50* (2013.01); *C07C 209/52* (2013.01)

(58) Field of Classification Search
CPC ....... C07C 45/71; C07C 29/14; C07C 29/147; C07F 5/025
See application file for complete search history.

(56) References Cited

FOREIGN PATENT DOCUMENTS

WO 2011/045605 A1 4/2011

OTHER PUBLICATIONS

Peuser et al., "CO2 and Formate Complexes of Phosphine/Borane Frustrated Lewis Pairs," Chemistry: A European Journal, 17: 9640-9650 (2011).
Binding et al., "Heterolytic activation of hydrogen using frustrated Lewis pairs containing tris (2,2',2"-perfluorobiphenyl) borane," Dalton Transactions, 41: 9061-9066 (2012).
International Search Report issued in corresponding International Patent Application No. PCT/EP2016/077007 dated Jan. 11, 2017.

*Primary Examiner* — Sikarl A Witherspoon
(74) *Attorney, Agent, or Firm* — Morgan, Lewis & Bockius LLP

(57) ABSTRACT

The present invention relates to a method for reducing unsaturated organic compounds chosen from the group formed by the aldehydes, the ketones, the imines, the carboxylic acids, the amides, and the esters with a boron formate having the formula (I) in the presence of a solvent and optionally a base.
The invention also relates to the use of the method for reducing unsaturated organic compounds chosen from the group formed by the aldehydes, the ketones, the imines, the carboxylic acids, the amides, and the esters according to the invention in the preparation of methanol, methylated amines, formaldehyde and alcohols; for the preparation of reactants for Suzuki coupling reactions; and in the manufacturing of vitamins, pharmaceutical products, glues, acrylic fibers, synthetic leather, pesticides.

16 Claims, 4 Drawing Sheets

USE FOR BORON FORMATES FOR REDUCING UNSATURATED ORGANIC FUNCTIONS

The present invention relates to a method for reducing unsaturated organic compounds chosen from the group formed by the aldehydes, the ketones, the imines, the carboxylic acids, the amides, and the esters with a boron formate having the formula (I) in the presence of a solvent and optionally a base.

The invention also relates to the use of the method for reducing unsaturated organic compounds chosen from the group formed by the aldehydes, the ketones, the imines, the carboxylic acids, the amides, and the esters according to the invention in the preparation of methanol, methylated amines, formaldehyde and alcohols; for the preparation of reactants for Suzuki coupling reactions; and in the manufacturing of vitamins, pharmaceutical products, glues, acrylic fibres, synthetic leather, pesticides.

Reduction chemical reactions, that is to say, reactions that reduce the formal oxidation number of an atom via transfer of electrons, are at the heart of contemporary molecular chemistry. In organic chemistry, these reductions are most often transfers of hydrides ($H^-$, $2\ e^- + 2\ H^+$) delivered from reactants based on elements of the main group such as boron and aluminium ($NaBH_4$, $B_2H_6$, $LiAlH_4$, for example) All these reducing agents are obtained via methods that are costly in terms of energy, most often at a high temperature from alkali hydrides such as NaH, LiH, and KH. The latter being produced industrially via reaction between the melted alkali metals and $H_2$ molecular hydrogen at high temperatures and pressures. FIG. 1 details the industrial method for preparation of the tetraborohydride of sodium $NaBH_4$ (TBHS) from borax, a natural source of the element boron.

The TBHS obtained in this manner is then used in reactions of reduction in particular of organic functions such as carbonyls (aldehydes and ketones) in order to give alcohols after acid hydrolysis. It should be noted that carboxylic acids are much more difficult to reduce with TBHS. Other hydrides such as the hydrides of aluminium ($LiAlH_4$ for example) or $BH_3$ can be used in order to reduce the organic functions such as carboxyls, including the ester, into alcohol after acid hydrolysis.

Nevertheless, it appears that the step of forming the hydrides changes the boron from a $B(OCH_3)_3$ highly oxidised state to an $NaBH_4$ highly reduced state, which necessarily leads to a large loss of energy because of the use of alkali hydrides with high energy.

Thus, the use of powerful reducing agents, such as the metal hydrides (aluminium hydride, borohydride, etc.) lead to highly exothermic reactions and do not provide favourable energy consumption during the reduction of organic compounds having an unsaturated function that can be reduced, such as the aldehydes, the ketones, the imines, the carboxylic acids, the amides, the esters, etc.

Certain scientists have reported the heterolytic cleavage of the hydrogen ($H_2$) by a Frustrated Lewis pair (Frustrated Les Pair or FLP), and the hydrogenation of $CO_2$ with the hydrogen obtained by said heterolytic cleavage in order to lead to formates of boron as illustrated in FIG. 8. In fact, when an FLP reacts with $H_2$, a species of the type ($BaseH^+$, $AcidH^-$) is formed and it is precisely this species that reacts with the $CO_2$ in order to lead to the boron formate ($BaseH^+$, $AcidOCHO^-$). The anionic boron formates thus obtained are not capable of activating the hydrogen ($H_2$) and are not therefore reducing species. In fact, an analysis of the literature rather reveals that the boron formates are only agents for the transfer of the formyl group [Organometallics 2013, 32, 2459-2462; Table 2 page 2461].

An alternative to the aforementioned metal hydrides can be the reducing systems that allow hydrogenation via transfer of organic compounds having an unsaturated function that can be reduced, with formic acid as the exclusive hydrogen donor. Indeed, numerous other donors are documented in the literature, in particular Hantzch ester, cyclohexadiene or isopropanol, but contrary to formic acid, the latter are not obtained by methods that use little energy and do not reintegrate the $CO_2$ into the energy cycle.

The hydrogenation via transfer is a hydrogenation technique in which the source of hydrogen is not dihydrogen, but another "hydrogen donor." In organic synthesis, the hydrogenation via transfer is useful for the reduction of polar unsaturated compounds such as, for example, the ketones, the aldehydes or the imines.

The main advantages of the hydrogenation via transfer using formic acid with respect to conventional hydrogenation (addition of a molecule of $H_2$) are: (i) the reactions are not carried out at high pressure of the flammable gas $H_2$ and do not therefore require special equipment; (ii) the hydrogen donors are generally easily accessible, inexpensive and easy to manipulate; (iii) the selectivity is better and the conditions are milder and (iv) the by-products of the reaction can most often be recycled.

The first major publication in the field of hydrogenation via transfer using formic acid dates to 1996. Indeed, Noyori et coll. reported that the prochiral ketones such as acetophenone can be reduced stereoselectively by using a chiral catalyst of ruthenium in the presence of formic acid and triethylamine [A. Fujii, S. Hashiguchi, N. Uematsu, T. Ikariya, R. Noyori, *J. Am. Chem. Soc.* 1996, 118, 2521-2522]. The enantiomeric excesses obtained are excellent and the yields most often greater than 90%. From a mechanistic point of view, the ruthenium formate [Ru]—OCHO leads, with the help of the ligand, to the ruthenium hydride [Ru]—H that allows the reduction of the carbonyl to be carried out in a concerted manner. These works lead to the boom in research on hydrogenation via transfer as an alternative to catalytic hydrogenation, and numerous catalytic systems derived from that of Noyori were developed for the reduction of the carbonyls and of the imines [G. Brieger, T. J. Nestrick, *Chem. Rev.* 1974, 74, 567-580; D. Wang, D. Astrue, *Chem. Rev.* 2015, 115, 6621-6686].

Besides the carbonyls and the imines, the nitro-aromatics such as the nitrobenzene $PhNO_2$ can be hydrogenated in the presence of formic acid. More precisely, Beller et coll. reported that the complex $Fe(BF_4)_2 \cdot 6H_2O$ in the presence of the ligand "tetraphos" $P(CH_2CH_2PPh_2)_3$ in ethanol at 40° C. allows the corresponding anilines to be obtained with yields that exceed 77% [G. Wienhofer, I. Sorribes, A. Boddien, F. Westerhaus, K. Junge, H. Junge, R. Llusar, M. Beller. *J. Am. Chem. Soc.* 2011, 133, 12875-12879]. It should be noted that the reduction is carried out without a base, which is rare for reductions of this type, but in a large excess of formic acid (4.5 equivalents of formic acid with respect to the substrate are necessary). The same group also demonstrated that the aromatic nitriles can be reduced into a primary amine by using Pd/C palladium on carbon as a catalyst in the presence of triethylammonium formate ($HCOO^-$, $HNEt_3^+$) in the THF at 40° C. The yields obtained range from 52 to 98% and only the aromatic nitriles can be reduced: the aliphatic nitriles remain intact in the previous conditions.

Besides the polarised organic functions mentioned above, the alkynes and the alkenes can also be hydrogenated by formic acid. An example was reported in 2011 by the group of Yin, Han et coll. who demonstrated that the reaction between Pd(0) (Pd(PEt$_3$)$_4$), an alkyne and a carboxylic acid leads to the hydropalladation product [R. Shen. T. Chen, Y. Zhao, R. Qiu, Y. Zhou, S. Yin, X. Wang, M. Goto, L. B. Han, *J. Am. Chem. Soc.* 2011, 133, 17037-17044]. This observation led them to establish a protocol for reduction of the alkynes into corresponding alkenes or alkanes. By using the precursor of palladium Pd$_2$(dba)$_3$ (dba=dibenzylideneacetone) with the ligand dppb (dppb=diphenylphosphinobutane) in the presence of formic acid in dioxane at 80° C., a large number of alkynes (terminal or non-terminal) are selectively converted into alkene having a (Z) configuration exclusively with good yields. When the dppb is replaced with the tricyclohexylphosphine PCy$_3$, the reduction is carried out until the alkane is obtained.

In 2008, Elsevier et coll. had already demonstrated that a complex of Pd(0) based on the N-heterocyclic carbene ligand IMes (IMes=1,3-bis(2,4,6-trimethylphenyl)imidazol-2-ylidene) allowed alkynes to be reduced into (Z) alkenes with good selectivity in the presence of a mixture of formic acid and triethylamine in the THF or the acetonitrile [P. Hauwert, G. Maestri, J. W. Sprengers. M. Catellani, C. J. Elsevier, *Angew. Chem. Int. Ed. Engl.* 2008, 47, 3223-3226].

Besides the reduction of unsaturated organic functions, the hydrogenation via transfer can be carried out directly on the hydride donor, namely the formic acid, in order to obtain methanol, for example. This type of reaction is called a dismutation reaction and is a particular case of hydrogenation via transfer when the donor also has a function that can be reduced.

The first works in the field were carried out in 2013 by Miller, Goldberg et coll. The authors demonstrated that the complex of iridium [Cp*Ir(bpy)(H$_2$O)](OTf)$_2$ (Cp*=pentamethylcyclopentadienyl, bpy=2,2'-bipyridine) allows yields of methanol that reach 12% to be obtained [A. J. Miller, D. M. Heinekey, J. M. Mayer, K. I. Goldberg, *Angew. Chem. Int. Ed. Engl.* 2013, 52, 3981-3984]. This figure represents the selectivity of the reaction for the formation of methanol as demonstrated in FIG. 2 according to the equation (3). This also means that 88% of the C—H bonds in H—COOH decompose into dihydrogen according to the equation (4) of FIG. 3 and not into methanol. This 12% selectivity is obtained at 60° C. in the presence of formic acid in an aqueous solution (C=12M). The conversion of the formic acid in this case is only 3%.

More recently, Cantat et al. demonstrated that by using a [Ru(COD)(methylallyl)$_2$] (COD=cyclooctadiene) complex of ruthenium combined with the tridentate ligand "triphos" CH$_3$C(CH$_2$PPh$_2$)$_3$ in the THF at 150° C., the selectivity (which corresponds here to the yield of methanol) can reach 26.7%. In the same conditions and in the presence of an acid additive (MSA, methane sulfonic acid), the yield exceeds 50%. The latter result currently represents the greatest yield of methanol obtained by dismutation of the formic acid [S. Savourey, G. Lefevre, J. C. Berthet, P. Thuery, C. Genre, T. Cantat, *Angew. Chem. Int. Ed. Engl.* 2014, 53, 10466-10470].

Lastly, Parkin et al. demonstrated in 2015 that compounds of molybdenum are capable of carrying out the reaction of dismutation of the formic acid [M. C. Neary, G. Parkin, *Chem. Sci.* 2015, 6, 1859-1865]. More precisely, the complex CpMo(CO)$_3$H (Cp=cyclopentadienyl) is the most efficient of the complexes evaluated and a selectivity of 21% is reported at 100° C. in the benzene.

The discovery of this new reaction then allowed the development of a new methodology of synthesis of methylamines via a sequence of formylation/hydrogenation via transfer [S. Savourey, G. Lefevre, J. C. Berthet, T. Cantat, *Chem. Commun.* 2014, 50, 14033-14036]. The catalytic system used in this case is the same as that developed by Cantat et coll. for the dismutation of formic acid and the reaction is limited to primary and secondary anilines.

This prior art reveals that the reducing systems currently known for promoting
    the reduction of the organic compounds comprising an unsaturated function that can be reduced, such as the aldehydes, the ketones, the imines, the carboxylic acids, the amides, the esters in the presence of formic acid, or
    the reaction of dismutation of the formic acid into methanol for example,
are based on metal systems, most often based on transition metals or noble metals, the cost, the abundance and the toxicity of which most often pose a problem. At present, there is no non-metal system that can carry out these transformations with formic acid as a hydride donor.

There is therefore a real need for a non-metal compound as a source of hydride that brings formic acid into play and allows the reduction of unsaturated organic compounds that can be reduced, such as the aldehydes, the ketones, the imines, the carboxylic acids, the amides, the esters.

There is also a real need for a non-metal compound as described above that brings into play formic acid both as a source of hydride and as a substrate to be reduced (dismutation) into methanol, into formaldehyde or into a methylated amine for example.

In particular, there is a real need for a non-metal compound as described above that does not contain:
    any alkaline earth metals from Group IIA of the Periodic Table of the Elements (such as magnesium and calcium);
    any transition metals from Group IB to VIIIB of the Periodic Table of the Elements (such as nickel, iron, cobalt, zinc, copper, rhodium, ruthenium, platinum, palladium, iridium);
    any rare earths having an atomic number between 57 and 71 (such as lanthanum, cerium, praseodymium, neodymium); or
    any actinides having an atomic number between 89 and 103 (such as thorium, uranium).

There is also a real need for a source of hydride that brings into play formic acid and allows the reduction of unsaturated organic compounds such as the aldehydes, the ketones, the imines, the carboxylic acids, the amides, and the esters, said source
    having an energy content that is less than the conventional metal hydrides for carrying out the reduction of the unsaturated organic compounds indicated above, and/or
    being inexpensive, and/or
    being not very toxic, and/or
    being safer than the known hydrides, for example by avoiding violent reactions with water (LiAlH$_4$ reacts violently with water while freeing hydrogen and must therefore be manipulate in strictly anhydrous conditions).

The goal of the present invention is to meet these needs by providing a method for reducing unsaturated organic compounds chosen from the group formed by the aldehydes, the ketones, the imines, the carboxylic acids, the amides, and the esters, characterised in that said unsaturated organic compound is reacted with a boron formate having the formula (I)

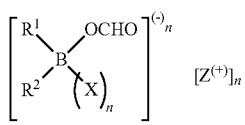

(I)

in which
- $R^1$ and $R^2$, independently of one another, are chosen from the group formed by a hydroxyl group, an alkoxy group, an alkyl group, an alkenyl group, an alkynyl group, an aryl group, a heteroaryl group, a heterocyclic group, a halogen atom, a silyl group, a siloxy group, a phosphino group, and an amino group, said alkyl, alkenyl, alkynyl, alkoxy, silyl, siloxy, aryl, phosphino and amino groups being optionally substituted; or
- $R^1$ and $R^2$ taken together with the boron atom to which they are bonded, form an optionally substituted heterocycle;
- X is chosen from the group formed by an atom of hydrogen, a halogen atom, a carboxylate group, a sulfonate group, a hydroxyl group, an alkoxy group, an alkyl group, an alkenyl group, an alkynyl group, an aryl group, a heteroaryl group, a heterocyclic group, a silyl group, a siloxy group, a phosphino group,
- Z is a cation chosen from the group formed by a protonated organic base having a pKa greater than 3.7; $Na^+$; $Li^+$; $K^+$; $Cs+$; tetraphenylphosphonium ($PPh_4^+$); tetramethylammonium ($NMe_4^+$); tetraethylammonium ($NEt_4^+$); tetrabutylammonium ($NBu_4^+$) and tetraphenylammonium ($NPh_4^+$);
- n is a whole number chosen from 0 and 1;

in the presence of a solvent and optionally an organic or inorganic base.

More particularly, the goal of the present invention is specifically to meet these needs by providing a method for reducing unsaturated organic compounds chosen from the group formed by the aldehydes, the ketones, the imines, the carboxylic acids, the amides, and the esters, characterised in that said unsaturated organic compound is reacted with a boron formate having the formula (I)

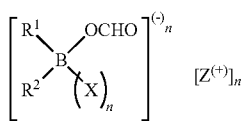

(I)

in which
- $R^1$ and $R^2$, independently of one another, are chosen from the group formed by a hydroxyl group, an alkoxy group, an alkyl group, an alkenyl group, an alkynyl group, an aryl group, a heteroaryl group, a heterocyclic group, a halogen atom, a silyl group, a siloxy group, a phosphino group, and an amino group, said alkyl, alkenyl, alkynyl, alkoxy, silyl, siloxy, aryl, phosphino and amino groups being optionally substituted; or
- $R^1$ and $R^2$ taken together with the boron atom to which they are bonded, form an optionally substituted heterocycle;
- X is chosen from the group formed by a halogen atom, a carboxylate group, a sulfonate group, a hydroxyl group, an alkoxy group, an alkyl group, an alkenyl group, an alkynyl group, a heteroaryl group, a heterocyclic group, a silyl group,
- Z is a cation chosen from the group formed by a protonated organic base having a pKa greater than 3.7 chosen from the group formed by triethylammonium ($HNEt_3^+$), di-isopropylethylammonium (i-$Pr_2EtNH^+$), 2,2,6,6-tetramethylpiperidinium ($TMPH^+$), and tricyclohexylphosphonium ($HPCy_3^+$); $Na^+$; $Li^+$; $K^+$; $Cs^+$; tetraphenylphosphonium ($PPh_4^+$); tetramethylammonium ($NMe_4^+$); tetraethylammonium ($NEt_4^+$); tetrabutylammonium ($NBu_4^+$) and tetraphenylammonium ($NPh_4^+$);
- n is a whole number equal to 1;

in the presence of a solvent and optionally an organic or inorganic base.

Thus, the boron formates having the formula (I) can be used for the reduction of organic compounds having an unsaturated function that can be reduced and is in particular polar chosen from the group formed by the aldehydes, the ketones, the imines, the carboxylic acids, the amides, and the esters, via transfer of hydride.

The method of the invention allows the aldehydes, the ketones, the carboxylic acids, and the esters to be reduced, into alcohols; the imines into amines; and the amides into amines or into alcohols.

Without the intent of being limited by the theory, in the method of the invention, it can be considered that in the boron formates having the formula (I), [B]—OCHO has reducing properties and can be considered to be equivalent to [B]—H. Thus, the reduction of the unsaturated organic compounds with the boron formates having the formula (I) allows the use of alkali hydride or of any other metal, for the formation of the B—H bond that allows the reduction, to be avoided.

The boron formates having the formula (I) in which n equal to 1, are not FLPs since they are conventional salts that comprise neither an acid nor a base in the Lewis sense. As a reminder, a frustrated Lewis pair is the combination of an acid and of a base in the Lewis sense, the combination of which in order to form a Lewis adduct is prevented for steric reasons.

The step of forming the hydride with the conventional alkali hydrides is thus eliminated. In the method of the invention, the hydride is generated, on demand, in situ, from the formate, in order to carry out the reduction of the unsaturated organic compounds.

More precisely, the method of the invention allows the step of forming the B—H bond from alkali hydrides to be eliminated by replacing the latter with the formation, in mild conditions, of a boron formate having the formula (i) and allows the latter to be used in reactions of reductions of organic functions.

The method of invention allows the negative environmental impact of the reduction reactions of organic chemistry that use boron hydrides generated from alkali hydrides to be reduced by substituting them with boron formates having the formula (I). One of the other advantages for such a technology is based on the use of formic acid as an equivalent of hydride, and said acid can be obtained via catalytic hydrogenation of $CO_2$, which therefore has the consequence of reintegrating the $CO_2$, a known greenhouse gas, into the energy cycle.

The reduction of the aforementioned unsaturated organic compounds that can be reduced using boron formates having the formula (I) without metal according to the method of the invention, avoids the disadvantages related to the use of the metals, in particular in terms of cost and toxicity.

Moreover, the method of the invention allows the reduction of the aforementioned unsaturated compounds with very good selectivity. In certain cases, the only product obtained after the method of reduction is the desired product.

In the context of the invention, a frustrated Lewis pair (Frustrated Lewis Pair or FLP) is defined as a combination, in the same reaction medium, of an acid and a base in the Lewis sense, the mutual interaction of which is impossible for steric reasons. A Lewis adduct designates a product of a reaction of addition between an acid and a base in the Lewis sense, for example:

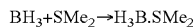

$BH_3 + SMe_2 \rightarrow H_3B.SMe_2$ $H_3B.SMe_2$ being said Lewis adduct.

In an FLP, the formation of Lewis adducts is not possible for steric reasons. For example, $B(C_6F_5)_3 + t\text{-}Bu_3P$ does not give $(C_6F_5)_3B.P(t\text{-}Bu)_3$. There is no interaction between $B(C_6F_5)_3$ which is the Lewis acid and $P(t\text{-}Bu)_3$ which is the Lewis base. A consequence of this property of "mutual non-interaction" involves taking advantage, in the same reaction medium and simultaneously, of the acid and base properties in the Lewis sense of the two compounds. This situation allowed the activation of the molecular hydrogen ($H_2$) "without metal", formerly the prerogative of the metals of transitions.

In the sense of the present invention, an "alkyl" group designates a saturated linear, branched or cyclic carbon radical, optionally substituted, comprising 1 to 12 atoms of carbon. Examples of a saturated linear or branched alkyl include the radicals methyl, ethyl, propyl, butyl, pentyl, hexyl, octyl, nonyl, decyl, undecyl, dodecanyl and their branched isomers. Examples of a cyclic alkyl include the radicals cyclopropyl, cyclobutyl, cyclopentyl, cyclohexyl, cycloheptyl, cyclooctyl, bicylco[2,1,1] hexyl, bicyclo[2,2,1] heptyl. The alkyl group can comprise for example 1 to 8 atoms of carbon.

"Alkenyl" or "alkynyl" means an unsaturated linear, branched or cyclic carbon radical, optionally substituted, said unsaturated carbon radical comprising 2 to 12 atoms of carbon comprising at least one double bond (alkenyl) or one triple bond (alkynyl). Examples of these include the radicals ethylenyl, propylenyl, butenyl, pentenyl, hexenyl, acetylenyl, propynyl, butynyl, pentynyl, hexynyl and their branched isomers. Examples of cyclic alkenyls include cyclopentenyl, cyclohexenyl. The alkenyl and alkynyl groups can comprise for example 2 to 8 atoms of carbon.

The alkyl, alkenyl, alkynyl groups can be optionally substituted with one or more hydroxyl groups; one or more alkoxy groups; one or more halogen atoms chosen from the atoms of fluorine, chlorine, bromine and iodine; one or more nitro groups (—$NO_2$); one or more nitrile groups (—CN); one or more aryl groups, with the alkoxy and aryl groups as defined in the context of the present invention.

The term "aryl" in general designates a cyclic aromatic substituent comprising 6 to 20 atoms of carbon. In the context of the invention, the aryl group can be monocyclic or polycyclic. Examples include the groups phenyl, benzyl and naphthyl. The aryl group can be optionally substituted with one or more hydroxyl groups, one or more alkoxy groups, one or more "siloxy" groups, one or more halogen atoms chosen from the atoms of fluorine, chlorine, bromine and iodine, one or more nitro groups (—$NO_2$), one or more nitrile groups (—CN), one or more alkyl groups, with the alkoxy, alkyl and siloxy groups as defined in the context of the present invention. The aryl group can comprise, for example, 6 to 10 atoms of carbon.

The term "heteroaryl" in general designates a monocyclic or polycyclic aromatic substituent comprising 5 to 12 members, including at least 2 atoms of carbon, and at least one heteroatom chosen from nitrogen, oxygen, boron, silicon, phosphorus and sulphur. The heteroaryl group can be monocyclic or polycyclic. Examples include the groups furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, pyrazolyl, oxazolyl, isoxazolyl, benzoxazolyl, thiazolyl, benzothiazolyl, isothiazolyl, pyridazinyl, pyrimidilyl, pyrazinyl, triazinyl, cinnolinyl, phtalazinyl, quinazolinyl. The heteroaryl group can be optionally substituted with one or more hydroxyl groups, one or more alkoxy groups, one or more halogen atoms chosen from the atoms of fluorine, chlorine, bromine and iodine, one or more nitro groups (—$NO_2$), one or more nitrile groups (—CN), one or more aryl groups, one or more alkyl groups, with the alkyl, alkoxy and aryl groups as defined in the context of the present invention.

The term "heterocycle or heterocyclic" in general designates a saturated or unsaturated monocyclic or polycyclic substituent, comprising 5 to 10 members, containing 1 to 4 heteroatoms chosen independently of each other, out of nitrogen, oxygen, boron, silicon, phosphorus and sulphur. Examples include borolane, borole, borinane, 9-borabicyclo[3.3.1]nonane (9-BBN), 1,3,2-benzodioxaborole (catecholborane or catBH), pinacholborane (pinBH), the substituents morpholinyl, piperidinyl, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl, isothiazolidinyl. The heterocycle can be optionally substituted with one or more hydroxyl groups, one or more alkoxy groups, one or more aryl groups, one or more halogen atoms chosen from the atoms of fluorine, chlorine, bromine and iodine, one or more nitro groups (—$NO_2$), one or more nitrile groups (—CN), one or more alkyl groups, with the alkyl, alkoxy and aryl groups as defined in the context of the present invention.

The term "alkoxy" means an alkyl group, as defined above, bonded by an atom of oxygen (—O-alkyl).

"Amino" group means a group having the formula —$NR^3R^4$, in which:
  $R^3$ and $R^4$ are, independently of one another, an alkyl group, an alkenyl group, an alkynyl group, an aryl group, a heteroaryl group, a heterocyclic group, a silyl group, a siloxy group, with the alkyl, alkenyl, alkynyl, aryl, heteroaryl, heterocyclic, silyl, siloxy groups, as defined in the context of the present invention; or
  $R^3$ and $R^4$, taken together with the atom of nitrogen to which they are bonded, form a heterocycle optionally substituted with one or more hydroxyl groups; one or more alkyl groups; one or more alkoxy groups; one or more halogen atoms chosen from the atoms of fluorine, chlorine, bromine and iodine; one or more nitro groups (—$NO_2$); one or more nitrile groups (—CN); one or more aryl groups; with the alkyl, alkoxy and aryl groups as defined in the context of the present invention.

Examples of these include diethylamino (—$NEt_2$), diphenylamino (—$NPh_2$), methylethylamino (—NMeEt), bis(t-rimethylsilyl)amino (—$N(SiCH_3)_2$).

"Phosphino" group means a group having the formula —$PR^5R^6$, in which:
  $R^5$ and $R^6$ are, independently of one another, an alkyl group, an alkenyl group, an alkynyl group, an aryl group, a heteroaryl group, a heterocyclic group, a silyl group, a siloxy group, with the alkyl, alkenyl, alkynyl, aryl, heteroaryl, heterocyclic, silyl, siloxy groups, as defined in the context of the present invention; or $R^5$ et $R^6$, taken together with the atom of phosphorus to which they are bonded, form a heterocycle optionally substituted with one or more hydroxyl groups; one or more alkyl groups; one or more alkoxy groups; one or more halogen atoms chosen from the atoms of fluorine, chlorine, bromine and iodine; one or more nitro groups (—$NO_2$); one or more nitrile groups (—CN); one or more aryl groups; with the alkyl, alkoxy and aryl groups as defined in the context of the present invention Examples of this include diethylphosphino (—$PEt_2$), diphenylphosphino (—$PPh_2$), methylethylphosphino (—PMeEt], bis(trimethylsilyl)phosphino (—$P(SiCH_3)_2$), dicyclohexylphosphino (—$PCy_2$).

Halogen atom means an atom chosen from the atoms of fluorine, chlorine, bromine and iodine.

The term sulfonate designates a group having the formula —$OSO_2R^7$, in which:
  $R^7$ is chosen from: a methyl group ($CH_3$), a trifluoromethyl group ($CF_3$), a toluene group (p-$CH_3C_6H_4$) and a benzene group ($C_6H_5$).

The group "carboxylate" designates a group having the formula —$OC(O)R^8$, in which:
  $R^8$ is chosen from: an atom of hydrogen, an alkyl group, an alkenyl group, an alkynyl group, an aryl group, a heteroaryl group, a heterocyclic group, a silyl group, a siloxy group, with the alkyl, alkenyl, alkynyl, aryl, heteroaryl, heterocyclic groups, as defined in the context of the present invention. More particularly, $R^8$ is chosen from an atom of hydrogen, an alkyl group, and an aryl group, said alkyl or aryl group. Examples of this include formate (—OC(O)H), acetate (—$OC(O)CH_3$), pivalate (—OC(O)tBu). Preferably, the carboxylate group is formate (—OC(O)H).

"Silyl" group means a group having the formula [—Si$(Y)_3$], in which each Y, independently of one another, is chosen from an atom of hydrogen; one or more halogen atoms chosen from the atoms of fluorine, chlorine, bromine and iodine; one or more alkyl groups; one or more alkoxy groups; one or more amino groups; one or more aryl groups; one or more siloxy groups; with the alkyl, alkoxy, aryl and siloxy groups as defined in the context of the present invention. Examples of this include trimethylsilyl (TMS), le triethylsilyl (TES), tert-butyldiphenylsilyl (TBDPS), tert-butyldimethylsilyl (TBS/TBDMS), triisopropylsilyl (TIPS), tri(trimethylsilyl)silyl or (($CH_3)_3Si)_3Si$— (TTMS), tri(tert-butyl)silyl or (($CH_3)_3C)_3Si$—.

"Siloxy" group means a silyl group, as defined above, bonded by an atom of oxygen (—O—Si$(Y)_3$) with Y as defined above. Examples of this include the trimethylsiloxy —$OSi(CH_3)_3$, the triethylsiloxy —$OSi(CH_2CH_3)_3$, the tert-butyldiphenylsiloxy —$OSi(tBuPh_2)_3$.

In the context of the invention, "protonolysis" means the cleavage of a chemical bond by Brønsted acids. Hydrolysis means the cleavage of a chemical bond by water.

According to a first specific embodiment of the invention, in the boron formate having the formula (I),
  $R^1$ and $R^2$, independently of one another, are chosen from the group formed by an alkyl group comprising 1 to 12 atoms of carbon; an aryl comprising 6 to 20 atoms of carbon, said alkyl and aryl groups being optionally substituted.

In this first embodiment, preferably, in the boron formate having the formula (I),
  $R^1$ and $R^2$, independently of one another, are chosen from the group formed by methyl, ethyl, propyl, butyl, pentyl, hexyl and their branched isomers, cyclohexyl, phenyl, benzyl. Even more preferably, $R^1$ and $R^2$, independently of one another, are chosen from the group formed by butyl and its branched isomers, and cyclohexyl.

According to a second specific embodiment of the invention, in the boron formate having the formula (I),
  $R^1$ and $R^2$ taken together with the atom of boron to which they are bonded, form a heterocycle comprising 5 to 10 members, said heterocycle being optionally substituted.

In this second embodiment, preferably, in the boron formate having the formula (I),
  $R^1$ and $R^2$ taken together with the atom of boron to which they are bonded, form a 9-borabicyclo[3.3.1]nonane (9-BBN), a 1,3,2-benzodioxaborole (catecholborane or catBH), or a pinacholborane (pinBH).

According to a third specific embodiment of the invention, in the boron formate having the formula (I),
  $R^1$ and $R^2$, independently of one another, are chosen from the group formed by an alkyl group comprising 1 to 12 atoms of carbon; said alkyl group being optionally substituted.

In this third embodiment, preferably, in the boron formate having the formula (I),
  $R^1$ and $R^2$, independently of one another, are chosen from the group formed by methyl, ethyl, propyl, butyl, pentyl, hexyl and their branched isomers, and cyclohexyl. Even more preferably, $R^1$ and $R^2$, independently of one another, are chosen from the group formed by butyl and its branched isomers, and cyclohexyl.

In all the alternatives and all the embodiments of the invention, in the boron formate having the formula (I), X can advantageously be chosen from the group formed by
  a halogen atom,
  an —OCHO carboxylate group,
  a sulfonate group having the formula —$OSO_2R^7$, in which $R^7$ is chosen from a methyl group ($CH_3$) or a trifluoromethyl group ($CF_3$), a toluene group (p-$CH_3C_6H_4$) or a benzene group ($C_6H_5$),
  a hydroxyl group,
  an alkoxy group, the alkyl group of which comprises 1 to 12 atoms of carbon chosen from the group formed by methyl, ethyl, propyl, butyl, pentyl, hexyl and their branched isomers, and
  an alkyl group comprising 1 to 12 atoms of carbon chosen from the group formed by methyl, ethyl, propyl, butyl, pentyl, hexyl and their branched isomers.

In all the alternatives and all the embodiments of the invention, in the boron formate having the formula (I), X can more advantageously be chosen from the group formed by an atom of hydrogen, a halogen atom, —OCHO and a sulfonate group having the formula —$OSO_2R^7$, in which $R^7$ is chosen from a methyl group ($CH_3$), a trifluoromethyl group ($CF_3$), a toluene group (p-$CH_3C_6H_4$) and a benzene group ($C_6H_5$).

In all the alternatives and all the embodiments of the invention, in the boron formate having the formula (I), X is more preferably chosen from the group formed by a halogen atom, —OCHO and a sulfonate group having the formula —$OSO_2R^7$, in which $R^7$ is chosen from a methyl group ($CH_3$), a trifluoromethyl group ($CF_3$), a toluene group (p-$CH_3C_6H_4$) and a benzene group ($C_6H_5$).

In all the alternatives and all the embodiments of the invention, in the boron formate having the formula (I), Z is a cation chosen from the group formed by a protonated base having a pKa greater than 3.7 chosen for example from the group formed by triethylammonium (HNEt$_3^+$), di-isopropylethylammonium (i-Pr$_2$EtNH$^+$), 2,2,6,6-tetramethylpiperidinium (TMPH$^+$), and tricyclohexylphosphonium (HPCy$_3^+$); Na$^+$; Li$^+$; K$^+$; Cs$^+$; tetraphenylphosphonium (PPh$_4^+$); tetramethylammonium (NMe$_4^+$); tetraethylammonium (NEt$_4^+$); tetrabutylammonium (NBu$_4^+$) and tetraphenylammonium (NPh$_4^+$).

In all the alternatives and all the embodiments of the invention, in the boron formate having the formula (I), Z is more preferably a cation chosen from the group formed by triethylammonium (HNEt$_3^+$), di-isopropylethylammonium (i-Pr$_2$EtNH$^+$), 2,2,6,6-tetramethylpiperidinium (TMPH$^+$), tricyclohexylphosphonium (HPCy$_3^+$), and Na$^+$. Even more preferably, Z can be a cation chosen from the group formed by triethylammonium (HNEt$_3^+$), tricyclohexylphosphonium (HPCy$_3^+$), and Na$^+$.

Preferably, in all the alternatives and all the embodiments of the invention, the boron formates having the formula (I) are [Et$_3$NH$^+$, BCy$_2$(OCHO)$_2^-$], [i-Pr$_2$EtNH$^+$, BCy$_2$(OCHO)$_2^-$], [Et$_3$NH$^+$, n-Bu$_2$B(OCHO)$_2^-$], [Et$_3$NH$^+$, BBN(OCHO)$_2^-$], [i-Pr$_2$EtNH$^+$, BBN(OCHO)$_2^-$], [Na$^+$, BBN(OCHO)$_2^-$], [Cy$_3$PH$^+$, BBN(OCHO)$_2^-$] and [TMPH$^+$, BBN(OCHO)$_2^-$]. More preferably, the boron formates having the formula (I) are [Et$_3$NH$^+$, BBN(OCHO)$_2^-$], [i-Pr$_2$EtNH$^+$, BBN(OCHO)$_2^-$], [Na$^+$, BBN(OCHO)$_2^-$], [Cy$_3$PH$^+$, BBN(OCHO)$_2^-$] and [TMPH$^+$, BBN(OCHO)$_2^-$].

In a fourth specific embodiment, when n=0, the boron formate has the general formula (Ia)

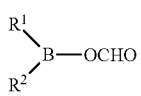

(Ia)

in which R$^1$ and R$^2$ are as defined above. The reduction of the unsaturated organic compounds thus requires the presence of an organic or inorganic base.

When the base is an inorganic base, this is a mineral compound having basic properties in the Brønsted sense. The inorganic base can be chosen from sodium carbonate (Na$_2$CO$_3$), potassium carbonate (K$_2$CO$_3$), sodium hydrogen carbonate (NaHCO$_3$), sodium hydride (NaH), and potassium hydride (KH).

The base is preferably organic.

The organic base can be chosen from:
the nitrogenous organic bases that are advantageously tertiary or secondary amines chosen from the group formed by, for example, triethylamine, trimethylamine, N-diisopropylethylamine (DIPEA), diethylisopropylamine (DIEA), 7-Methyl-1,5,7-triazabicyclo[4.4.0]dec-5-ene (MTBD), 1,8-diazabicyclo[5.4.0]undec-7-ene (DBU), 1,4-diazabicyclo[2.2.2]octane (DABCO), N-methylpiperidine, 2,2,6,6-tetramethylpiperidine (TMP), piperidine, N-methylaniline, pyrrolidine, morpholine and diisopropylamine (DIPA).
the phosphorus-containing organic bases that can be alkyl or aryl phosphines chosen from the group formed by, for example, triphenylphosphine, 2,2'-bis(diphenylphosphino)-1,1'-binaphthyl (BINAP), triisopropylphosphine, 1,2-bis(diphenylphosphino)ethane (dppe), tricyclohexylphosphine (PCy$_3$); the aza-phosphines chosen from, for example, 2,8,9-triisopropyl-2,5,8,9-tetraaza-1-phosphabicyclo[3.3.3]undecane (BV$^{Me}$) and 2,8,9-triisobutyl-2,5,8,9-tetraaza-1-phosphabicyclo[3.3.3]undecane (BV$^{iBu}$);
the carbonaceous bases for which the protonation takes place on an atom of carbon, chosen advantageously from the N-heterocyclic carbenes resulting from an imidazolium salt, said carbenes being, for example, chosen from the group formed by the salts of 1,3-bis(2,6-diisopropylphenyl)-1H-imidazol-3-ium (also called IPr), 1,3-bis(2,6-diisopropylphenyl)-4,5-dihydro-1H-imidazol-3-ium (also called s-IPr), 1,3-bis(2,4,6-trimethylphenyl)-1H-imidazol-3-ium (also called IMes), 1,3-bis(2,4,6-trimethylphenyl)-4,5-dihydro-1H-imidazol-3-ium (also s-IMes), 4,5-dichloro-1,3-bis(2,6-diisopropylphenyl)-1H-imidazol-3-ium (also called Cl$_2$—IPr), 1,3-di-tert-butyl-1H-imidazol-3-ium (also called ItBu), and 1,3-di-tert-butyl-4,5-dihydro-1H-imidazol-3-ium (also called s-ItBu), said salts being in the form of salts of chloride or of tetraphenylborate, for example.

Examples of N-heterocyclic carbenes are shown in FIG. 4.

Preferably, the organic base is a nitrogenous organic base chosen from the group formed by triethylamine, trimethylamine, N-diisopropylethylamine (DIPEA), diethylisopropylamine (DIEA), 7-Methyl-1,5,7-triazabicyclo[4.4.0]dec-5-ene (MTBD), 1,8-diazabicyclo[5.4.0]undec-7-ene (DBU), 2,2,6,6-tetramethylpiperidine (TMP) and diisopropylamine (DIPA).

In this fourth specific embodiment; the quantity of base is from 0.05 to 3 molar equivalents preferably from 0.5 to 1.5 molar equivalents inclusive, with respect to the boron formate having the formula (Ia).

In a fifth specific embodiment of the invention, when n=1, the boron formate has the general formula (Ib)

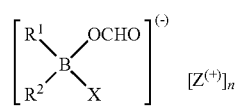

(Ib)

in which R$^1$, R$^2$, X and Z are as defined above. The reduction of the unsaturated organic compounds does not therefore require the presence of a base.

As already indicated, the boron formates having the formula (Ib) are not frustrated Lewis pairs (Frustrated Lewis Pair or FLP). They are conventional salts comprising a cationic residue (Z$^+$) and an anionic residue (the boron formate).

In all the embodiments and alternative of the invention, when it is necessary, in the method for reduction according to the invention, an additive can also be used to solubilise the starting reactants. In the sense of the invention, additive means any compound capable of improving the solubility of the reactants used in the method for reduction of the invention. These additives are introduced, for example, when the alkali salts of boron formate having the formula (I) are used (for example Na$^+$ or K$^+$). These additives can be chosen, for example, from:
the crown ethers chosen from the group formed by 12-crown-4, 15-crown-5, 18-crown-6, dibenzo-18-crown-6, benzo-18-crown-6, benzo-15-crown-5, and dibenzo-15-crown-5;

the aza-crowns chosen from the group formed by 1,4,7,10-tetraazacyclododecane (cyclen), 1,4,7,10,13,16-hexaazacyclooctadecane (hexacyclen), and diaza-18-crown-6;

the crown thioethers chosen from the group formed speak 1,5,9,13-tetrathiacyclohexadecane (16-Ane-$S_4$), and 1,4,7,10,13,16-hexathiacyclooctadecane (18-Ane-$S_6$).

The operating conditions described for the method for reduction of the aforementioned unsaturated organic compounds by the formates having the formula (I) according to the invention, apply to all the embodiments and alternatives of the invention, including the boron formates having the formula (Ia) and (Ib).

The quantity of the unsaturated organic compounds to be reduced is from 0.5 to 2 molar equivalents, preferably from 0.5 to 1.1 molar equivalents, inclusive, with respect to the boron formate having the formula (I).

The method for reduction by the formates having the formula (I) can take place in one or a mixture of at least two solvents. The solvent can be chosen from the group formed by:
the ethers chosen from diethyl ether, THF, diglyme, 1,4-dioxane;
the hydrocarbons chose from benzene, or toluene;
the nitrogenous solvents chosen from pyridine, or acetonitrile;
the sulfoxides chosen from dimethyl sulfoxide;
the alkyl halides chosen from chloroform, or methylene chloride; and
a supercritical fluid chosen from supercritical $CO_2$.

The method for reduction is preferably carried out in an aprotic polar solvent such as THF or acetonitrile and more preferably in acetonitrile.

The method for reduction of the invention takes place at a temperature greater than 25° C., preferably between 30 and 200° C., more preferably between 50 and 180, even more preferably between 80 and 130° C., inclusive.

The duration of the reduction depends on the type of bond to be reduced and on the boron formate having the formula (I) used to carry out the reduction. In general, the duration of the method for reduction is from 30 min to 72 h, preferably from 2 h to 24 h, inclusive.

When an additive is used, the quantity of additive is from 1 to 2 molar equivalents preferably from 1 to 1.5 molar equivalents inclusive, with respect to the boron formate having the formula (I).

The unsaturated organic compounds chosen from the group formed by the aldehydes, the ketones, the imines, the carboxylic acids, the amides, and the esters to be reduced are, in general, marketed compounds or can be prepared by any method known to a person skilled in the art.

The method for reduction of the invention generates a gas pressure resulting from the formation of carbon dioxide and optionally dihydrogen. The reaction can thus take place under the pressure of the gases formed or under atmospheric pressure while recovering the gases, for example in a burette. This or these gas(es) can be reused to prepare the formic acid or one of its derivatives for example in order to carry out the reduction of the $CO_2$ at $2e^-$.

As already indicated, the method of the invention allows the aldehydes, the ketones, the carboxylic acids and the esters to be reduced, into alcohols; the imines into amines; and the amides into amines or into alcohols. These reactions are illustrated in FIG. 6 with $R^1$, $R^2$ and $R^3$ as defined above.

When in the boron formate having the formula (I) or (Ib), X is —OCHO or when the boron formate has the formula (Ia) and the desired reduction product is methanol, formaldehyde or a methylated amine, the addition of an unsaturated substrate is not necessary since these products can be obtained in dismutation conditions. Dismutation forms a sixth specific embodiment of the invention. Examples of a dismutation reaction are shown in FIG. 7. Indeed, in dismutation conditions, the unsaturated substrate that can be reduced is the formate that is already present in the boron formate having the formula (I) or (Ib) or (Ia). In the context of the invention, "dismutation" means that the substrate to be reduced and the source of hydride are the same residue, namely, the —OCHO formate.

In the case of the dismutation of formic acid into a methylated amine, a primary or secondary amine must be introduced into the reaction medium if said amine is not already included in the boron formate having the formula (Ib) in protonated form (and in this specific case, $Z^+$ is thus a protonated primary or secondary amine). This allows convergence towards obtaining the methylated amine rather than towards methoxyborane.

Without the intent of being limited by a theory, in dismutation conditions, the atom of boron present in the boron formate having the formula (I) or (Ib) allows the transfer of hydride from the —OCHO formate to the boron with the formation of B—H, then the transfer of the hydride of the boron to the formate to carry out the reduction. Thus, a portion of the formate is used to provide the hydrides and a portion is used as a substrate in order to be reduced.

In the case of the dismutation reaction, the thermolysis at a temperature greater than 25° C., preferably between 30 and 200° C., more preferably between 50 and 180, even more preferably between 80 and 130° C., inclusive, of the boron formate having the formula (I) or (Ib) gives the reduction product. Obtaining methanol and formaldehyde requires hydrolysis (addition of water) at the end of the reaction, followed by distillation and/or transfer under vacuum. In the case of methylated amines, the latter can be recovered directly via distillation and/or transfer, under vacuum, of the raw reaction product. If the methylated amine is not a volatile compound, column chromatography allows it to be isolated in pure form.

The boron formates having the formula (I), (Ia) and (Ib) can be prepared by a method in which an organoborane having the formula (II)

(II)

in which $R^1$, $R^2$ and X are as defined above, is reacted with formic acid, or with one of its derivatives having the formula $HCO_2Z$ in which Z is as defined above, or with a mixture of formic acid and at least one of its derivatives;
optionally in the presence of an organic or inorganic base.

One of the advantages of this method is in the use of formic acid that can be obtained via catalytic hydrogenation of $CO_2$, which has the consequence of reintegrating the $CO_2$, a known greenhouse gas, into the energy cycle.

Moreover, the use of the boron formates having the formula (I), (Ia) or (Ib) can have other advantages, in particular:
The formic acid used for their preparation is liquid in normal temperature and pressure conditions, which makes it easy to transport with lower costs (and thus lower risks) than the transport of gas such as hydrogen.

This is particularly advantageous when the production of the formic acid and the method for preparing the boron formates are carried out in two distinct locations. This step is therefore the same as storing the hydrogen in the form of formic acid.

Formic acid is non-toxic in a diluted solution (concentration less than 85% by weight in the water) and is therefore a benign reactant. This should be compared in particular to the step of forming the sodium hydride presented in FIG. 1, or the melted sodium and the hydrogen are reacted. The additional costs related to the drastic safety measures required for the installation of this type of method are indeed significant.

The organoboranes having the formula (II) used for the preparation of the boron formates having the formula (I), (Ia) or (Ib) are marketed, or easily prepared by a person skilled in the art from marketed, inexpensive reactants. A contrario, when metals are used, the ligands used to stabilise them are costly and their preparation most often requires multiple synthesis steps.

All the definitions, embodiments and preferred embodiments described above for the boron formates having the formula (I), (Ia) or (Ib) in particular with regard to the substituents $R^1$, $R^2$, X, also apply to the organoboranes having the formula (II).

The operating conditions described for the method for preparing formates having the formula (I), also apply to all the embodiments and alternatives of the invention, including the preparation of the boron formates having the formula (Ia) and (Ib).

In the method for preparing the boron formates having the formula (I), (Ia) or (Ib), the organoborane having the formula (II) is, preferably, chosen from the group formed by dicyclohexylborane, dicyclohexylborane triflate ($Cy_2BOSO_2CF_3$), iododicyclohexylborane, chlorodicyclohexylborane, dibutylborane, dibutylborane methanesulfonate (n-$Bu_2BOSO2Me$), 9-borabicyclo[3.3.1]nonane (9-BBN), B-methoxy-9-borabicyclo[3.3.1]nonane (B-OMe-9-BBN), B-iodo-9-borabicyclo[3.3.1]nonane (B-I-9-BBN), B-bromo-9-borabicyclo[3.3.1]nonane (B-Br-9-BBN), B-benzyl-9-borabicyclo[3.3.1]nonane, Me-TBD-BBN$^+$I.

The method for preparing boron formates having the formula (I), (Ia) or (Ib) can take place in the presence of an organic or inorganic base.

When the base is an inorganic base, this is a mineral compound having basic properties in the Brønsted sense. The inorganic base can be chosen from sodium carbonate ($Na_2CO_3$), potassium carbonate ($K_2CO_3$), sodium hydrogen carbonate ($NaHCO_3$), sodium hydride (NaH), and potassium hydride (KH).

The base is preferably organic.

The organic base can be chosen from:
the nitrogenous organic bases that are advantageously tertiary or secondary amines chosen from the group formed by, for example, triethylamine, trimethylamine, N-diisopropylethylamine (DIPEA), diethylisopropylamine (DIEA), 7-Methyl-1,5,7-triazabicyclo[4.4.0]dec-5-ene (MTBD), 1,8-diazabicyclo[5.4.0]undec-7-ene (DBU), 1,4-diazabicyclo[2.2.2]octane (DABCO), N-methylpiperidine, 2,2,6,6-tetramethylpiperidine (TMP), piperidine, N-methylaniline, pyrrolidine, morpholine and diisopropylamine (DIPA).
the phosphorus-containing organic bases that can be alkyl or aryl phosphines chosen from the group formed by, for example, triphenylphosphine, 2,2'-bis(diphenylphosphino)-1,1'-binaphthyl (BINAP), triisopropylphosphine, 1,2-bis(diphenylphosphino)ethane (dppe), tricyclohexylphosphine ($PCy_3$); the aza-phosphines chosen from, for example, 2,8,9-triisopropyl-2,5,8,9-tetraaza-1-phosphabicyclo[3.3.3]undecane ($BV^{Me}$) and 2,8,9-triisobutyl-2,5,8,9-tetraaza-1-phosphabicyclo[3.3.3]undecane ($BV^{iBu}$);
the carbonaceous bases for which the protonation takes place on an atom of carbon, chosen advantageously from the N-heterocyclic carbenes resulting from an imidazolium salt, said carbenes being, for example, chosen from the group formed by the salts of 1,3-bis(2,6-diisopropylphenyl)-1H-imidazol-3-ium (also called IPr), 1,3-bis(2,6-diisopropylphenyl)-4,5-dihydro-1H-imidazol-3-ium (also called s-IPr), 1,3-bis(2,4,6-trimethylphenyl)-1H-imidazol-3-ium (also called IMes), 1,3-bis(2,4,6-trimethylphenyl)-4,5-dihydro-1H-imidazol-3-ium (also s-IMes), 4,5-dichloro-1,3-bis(2,6-diisopropylphenyl)-1H-imidazol-3-ium (also called $Cl_2$—IPr), 1,3-di-tert-butyl-1H-imidazol-3-ium (also called ItBu), and 1,3-di-tert-butyl-4,5-dihydro-1H-imidazol-3-ium (also called s-ItBu), said salts being in the form of salts of chloride or of tetraphenylborate, for example.

Examples of N-heterocyclic carbenes are shown in FIG. 4.

Preferably, the organic base is a nitrogenous organic base chosen from the group formed by triethylamine, trimethylamine, N-diisopropylethylamine (DIPEA), diethylisopropylamine (DIEA), 7-Methyl-1,5,7-triazabicyclo[4.4.0]dec-5-ene (MTBD), 1,8-diazabicyclo[5.4.0]undec-7-ene (DBU), 2,2,6,6-tetramethylpiperidine (TMP) and diisopropylamine (DIPA).

When necessary, an additive can also be used to solubilise the starting reactants. In the sense of the invention, additive means any compound capable of improving the solubility of the reactants used in the method for preparing the boron formates having the formula (I). These additives can be chosen, for example, from:
the crown ethers chosen from the group formed by 12-crown-4 (12-C-4), 15-crown-5 (15-C-5), 18-crown-6 (18-C-6), dibenzo-18-crown-6 (DB18-C-6), benzo-18-crown-6 (B 18-C-6), benzo-15-crown-5 (C15-C-5), and dibenzo-15-crown-5 (DB15-C-5);
the aza-crowns chosen from the group formed by 1,4,7,10-tetraazacyclododecane (cyclen), 1,4,7,10,13,16-hexaazacyclooctadecane (hexacyclen), and diaza-18-crown-6;
the crown thioethers chosen from the group formed speak 1,5,9,13-tetrathiacyclohexadecane (16-Ane-$S_4$), and 1,4,7,10,13,16-hexathiacyclooctadecane (18-Ane-$S_6$).

The organoboranes having the formula (II) can, if necessary, be immobilised on heterogeneous substrates in order to ensure their easy separation and/or their recycling. Said heterogeneous substrates can be chosen from the substrates containing silica gel or plastic polymers such as, for example, polystyrene; the carbon substrates chosen from carbon nanotubes; silica carbide; alumina; and magnesium chloride ($MgCl_2$).

The formic acid or one of its derivatives as defined above can be prepared by any method known to a person skilled in the art. In the present disclosure, methods known to be capable of carrying out this step were described. Preferably, the formic acid is prepared via electro-reduction at 2e$^-$ or catalytic hydrogenation of the $CO_2$ as shown in FIG. 5. The derivatives of the formic acid are prepared from the latter or obtained directly for example via hydrogenation of the $CO_2$.

The catalytic hydrogenation of the $CO_2$ requires the use of a base in order to move the equilibrium towards the formation of the formate salt. Thus, when the catalytic hydrogenation of the $CO_2$ is chosen and in the method of the invention, a base is used, the two reactions can be carried out successively in the same reactor.

If the electro-reduction of the $CO_2$ at $2e^-$ is chosen to prepare the formic acid and in the method for preparing boron formates having the formula (I), a base is used, the two reactions can be carried out successively in the same reactor. The base will then have to be added.

The reduction of the $CO_2$ at $2e^-$, is preferably carried out according to the most selective methods currently known. For example, the catalytic hydrogenation of the $CO_2$ can be carried out according to the protocol of Nozaki et coll. [R. Tanaka, M. Yamashita. K. Nozaki, *J. Am. Chem. Soc.* 2009, 131, 14168-14169] and allows potassium formate to be recovered. The electro-reduction can be carried out according to the conditions of Shibata et coll. or of Hori et coll. [Y. Hori, H. Wakebe, T. Tsukamoto, O. Koga, *Electrochim. Acta* 1994, 39, 1833-1839; N. Furuya, T. Yamazaki, M. Shibata, *J. Electroanal. Chem.* 1997, 431, 39-41]

It should be noted that the electro-reductions are dependent on a large number of parameters such as the nature of the reactor, the electrodes, the electrolyte or the electrocatalyst used. These notions and the various systems allowing formic acid or one of its derivatives to be obtained are discussed in the reviews of Olah et coll., of Leung, Xuan et coll. and of Kenis et coll. [A. Goeppert, M. Czaun, J. P. Jones, G. K. Surya Prakash, G. A. Olah. *Chem. Soc. Rev.* 2014, 43, 7995-8048; H.-R. M. Jhong, S. Ma, P. J. A. Kenis, *Curr. Opin. Chem. Eng.* 2013, 2, 191-199; X. Lu, D. Y. C. Leung, H. Wang, M. K. H. Leung, J. Xuan, *ChemElectroChem* 2014, 1, 836-849]. The formic acid or one of its derivatives (formate of sodium, potassium, lithium, caesium, ammonium for example) thus formed can then be used in the step of reduction.

The various reactants used in the method for preparing the formates having the formula (I) (i.e. the organoboranes having the formula (II), the formic acid or one of its derivatives, the base, the additive) are, in general, marketed compounds or can be prepared by any method known to a person skilled in the art.

The quantity of the organoborane having the formula (II) is from 0.05 to 1 molar equivalent, preferably from 0.5 to 1 molar equivalent inclusive, with respect to the formic acid or to its derivative(s), or to a mixture of formic acid and of at least one of its derivatives.

When a base is used, the quantity of base is from 0.05 to 3 molar equivalents preferably from 0.5 to 1.5 molar equivalents inclusive, with respect to the formic acid or to its derivative(s), or to a mixture of formic acid and of at least one of its derivatives.

When an additive is used, the quantity of additive is from 1 to 2 molar equivalents preferably from 1 to 1.5 molar equivalents inclusive, with respect to the derivative(s) of the formic acid or to a mixture of formic acid and of at least one of its derivatives.

The number of equivalents of the organoborane having the formula (II), of the base and of the additive are actually calculated with respect to the number of equivalents of $HCOO^-$. For example, in the case of a mixture of formic acid with at least one of its derivatives for example such as, an HCOOH/HCOONa mixture (1:1), the number of formal equivalents of $HCOO^-$ is 2.

The method for preparing the boron formates having the formula (I), (Ia) or (Ib) can take place at a temperature between $-78°$ C. and $150°$ C., for example between 0 and $100°$ C., for example between 0 and $30°$ C., for example between 15 and $25°$ C., inclusive.

The duration of the reaction depends on the rate of conversion of the formic acid. The reaction can be carried out for a duration of 5 minutes to 200 hours, preferably of 10 minutes to 24 hours, inclusive.

The method for preparing boron formates having the formula (I), (Ia) or (Ib) can be carried out in pure formic acid, in one of the derivatives of formic acid if the latter is liquid or by using one or a mixture of at least two solvents. The solvent can be chosen from the group formed by:
  the ethers, preferably, diethyl ether, THF, diglyme, 1,4-dioxane;
  the hydrocarbons, preferably, benzene, or toluene;
  the nitrogenous solvents, preferably, pyridine, or acetonitrile;
  the sulfoxides, preferably, dimethyl sulfoxide;
  the alkyl halides, preferably, chloroform, or methylene chloride; and
  a supercritical fluid, preferably; supercritical $CO_2$.

The method for preparing the boron formate is preferably carried out in an aprotic solvent such as THF, benzene or toluene.

The object of the invention is also, the use of the method for reduction of unsaturated organic compounds chosen from the group formed by the aldehydes, the ketones, the imines, the carboxylic acids, the amides, and the esters with the boron formates having the formula (I), (Ia) or (Ib) according to the invention,
  for the preparation of methanol, methylated amines having the formula $R^1R^2N$—$CH_3$, formaldehyde and alcohols having the formula $R^1CH_2OH$ with $R^1$ and $R^2$ as defined above;
  for the preparation of reactants for Suzuki coupling reactions,
  in the manufacturing of vitamins, pharmaceutical products, glues, acrylic fibres, synthetic leather, pesticides.

Another object of the invention relates to a method for preparing methanol comprising (i) a step of reducing formic acid or one of its esters having the formula $HCO_2R^8$ in which $R^8$ is as defined above, with a boron formate having the formula (I), (Ia) or (Ib) according to the method of the invention, and optionally (ii) a step of hydrolysis. After the hydrolysis, optionally distillation or concentration under vacuum can be necessary.

The object of the invention is also, a method for preparing methylated amines having the formula $R^1R^2N$—$CH_3$ with $R^1$ and $R^2$ as defined above, comprising (i) a step of reducing formic acid in the presence of a primary amine or a secondary amine, with a boron formate having the formula (I), (Ia) or (Ib) according to the method of the invention, and (ii) distillation or concentration under vacuum or column chromatography.

The object of the invention is also, a method for preparing formaldehyde, comprising a step of reducing formic acid or one of its esters having the formula $HCO_2R^8$ in which $R^8$ is as defined above, with a boron formate having the formula (I), (Ia) or (Ib) according to the method of the invention, and optionally (ii) a step of hydrolysis. After hydrolysis, optionally distillation or concentration under vacuum can be necessary.

The object of the invention is also, a method for preparing an alcohol having the formula $R^1CH_2OH$ with $R^1$ as defined above, comprising (i) a step of reducing an unsaturated organic compound chosen from the group formed by the aldehydes, the carboxylic acids, and the esters with a boron formate having the formula (I), (Ia) and (Ib) according to the method of the invention, and optionally (ii) a step of hydrolysis. After hydrolysis, optionally distillation or concentration under vacuum can be necessary.

The method for reduction of an unsaturated organic compound chosen from the group formed by the aldehydes, the ketones, the imines, the carboxylic acids, the amides, and the esters, with a boron formate having the formula (I), (Ia), (Ib) according to the invention can also be used for manufacturing vitamins, pharmaceutical products, glues, acrylic fibres, synthetic leather, pesticides.

Thus, the invention also relates to a method for manufacturing vitamins, pharmaceutical products, glues, acrylic fibres, synthetic leather, pesticides comprising a step of reduction of an unsaturated organic compound chosen from the group formed by the aldehydes, the ketones, the imines, the carboxylic acids, the amides, and the esters, with a boron formate having the formula (I), (Ia) or (Ib) according to the method of the invention.

The various uses described for the method for reducing the aforementioned unsaturated organic compound with the boron formates having the formula (I) according to the invention, applies in the same way to the boron formates having the formula (Ia) and (Ib).

Other advantages and features of the present invention will be clear upon reading the examples below that are given for informational purposes and are non-limiting and the appended figures.

EXAMPLES

Figure 1:
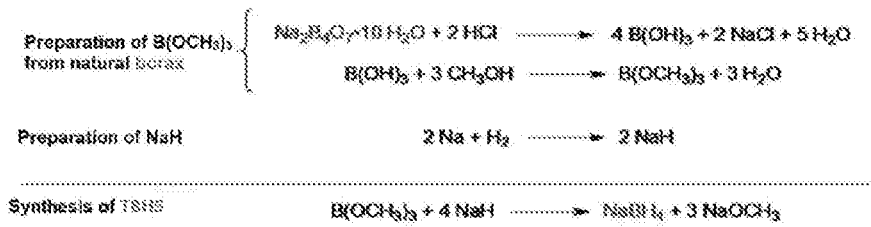
FIG. 1 shows details of the industrial method for preparing $NaBH_4$ sodium tetraborohydride (TBHS) from borax, a natural source of the element boron.
Figure 2:
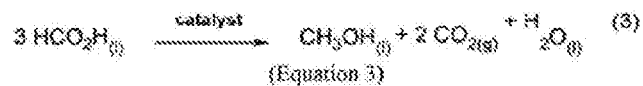
FIG. 2 shows the dismutation of formic acid into $CO_2$ and methanol.
Figure 3:
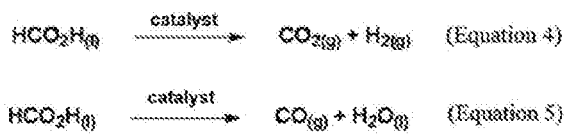
FIG. 3 shows two reactions of decomposition of formic acid that compete with the reaction of dismutation of formic acid into methanol and $CO_2$. These two reactions are: the dehydrogenation of formic acid into $CO_2$ and $H_2$ (Equation (4)) and the dehydration of formic acid into CO and $H_2O$ (Equation (5))
Figure 4:
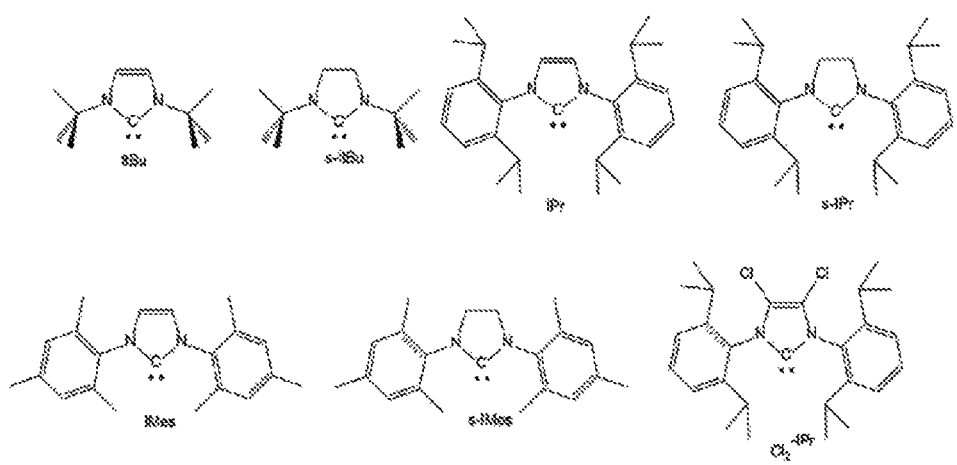
FIG. 4 shows examples of N-heterocyclic carbenes.
Figure 5:
FIG. 5 shows the preparation of formic acid via electro-reduction at $2e^-$ or catalytic hydrogenation of $CO_2$.
Figure 6:
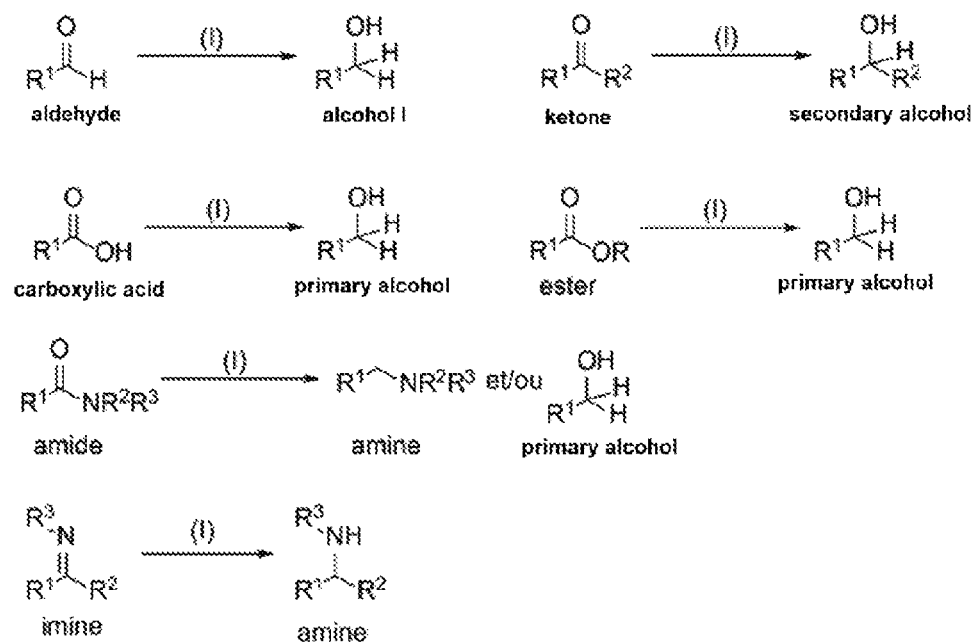
FIG. 6 shows the reduction of aldehydes, ketones, carboxylic acids and esters, into alcohols; imines into amines; and amides into amines or into alcohols with $R^1$, $R^2$, and $R^3$ as defined above.
Figure 7:
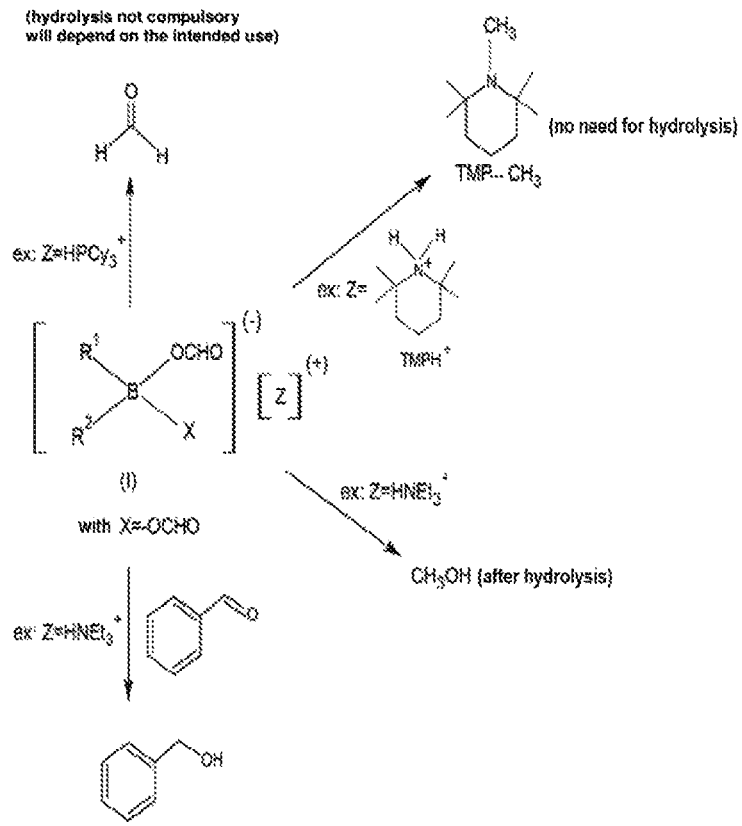
FIG. 7 shows an example of reduction of an aldehyde into a primary alcohol according to the method of the invention, as well as the particular case of dismutation of boron formate having the formula (I) or (Ib) into methanol, into formaldehyde and a methylated amine.
Figure 8:
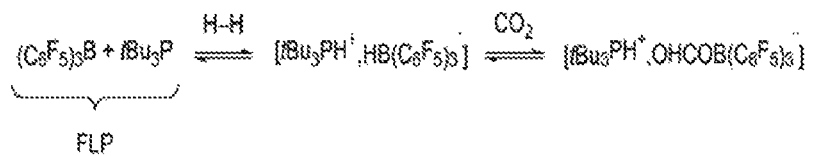
FIG. 8 shows the heterolytic cleavage of $H_2$ with an FLP, namely $(B(C_6F_5)_3+t-Bu_3P)$, in order to form a salt, namely a phosphonium $(PH^+)$ of boratohydride $(BH^-)$, followed by the hydrogenation of $CO_2$ by said salt in order to lead to the corresponding boron formate.

A set of results is presented below, giving examples of syntheses of boron formates and of their uses in reactions of reduction of aldehydes but also of dismutation into methoxyboranes and of methylation of amines. The yields are obtained by integration of the signals of the reduced product with respect to those of mesitylene or of diphenylmethane ($Ph_2CH_2$) used as an internal standard.

In the case of the preparation of the methanol via the reaction of dismutation of the formic acid, the yields are calculated while respecting the stoichiometry of the reaction of dismutation namely that at best, 3 moles of formic acid give at most 1 mol of methanol.

Yield of reduction product:

$$\rho(\text{reduction}) = \frac{n(\text{reduced product})}{n_0(\text{substrate to be reduced})}$$

Yield of methanol:

$$\rho(\text{MeOH}) = \frac{3 \times n(\text{MeOH})}{n_0(\text{HCOOZ})}$$

Yield of methoxyborane:

$$\rho(\text{MeOB}R^1R^2) = \frac{3 \times n(\text{MeOB}R^1R^2)}{n_0(\text{HCOOZ})}$$

Yield of methylated amine:

$$\rho(\text{MeN}R^1R^2) = \frac{n(\text{MeN}R^1R^2)}{n_0(\text{HN}R^1R^2)}$$

n(reduced product): quantity of matter of reaction product determined by $^1$H NMR with respect to mesitylene $n_0$(substrate): quantity of matter of substrate that can be reduced initially introduced.

n(MeOH): quantity of matter determined by $^1$H NMR with respect to mesitylene.

$n_0$(MeOB$R^1R^2$): quantity of matter of methoxyborane determined by $^1$H NMR with respect to mesitylene.

n(MeN$R^1R^2$): quantity of matter of methylated amine determined by $^1$H NMR with respect to mesitylene or diphenylmethane.

$n_0$(HN$R^1R^2$): quantity of matter of amine initially introduced in the form of free amine or as Z in the boron formates having the formula (Ib)

$n_0$(HCOOZ)=$n_0$(HCOOH)+$n_0$(HCOOM): total quantity of matter of formic acid (HCOOH) and its derivatives (HCOOM, M as defined above) initially introduced.

Protocol of Preparation of the Boron Formates Having the Formula (I)

The boron formate having the formula (I) can be prepared according to the following experimental protocol:

1. Under an inert atmosphere, in a glove box, the organoborane having the formula (II), the formic acid or one of its derivatives, or a mixture of formic acid and of at least one of its derivatives and optionally, the solvent and/or the base and/or the additive are introduced into a Schlenk tube that is then sealed by a J. Young valve. The order of introduction of the reactants is not important.
2. The reaction mixture is then stirred at a temperature between 0 and 30° C. (preferably at the ambient temperature, that is to say 20±5° C.) until the total conversion of the formic acid (from 5 minutes to 24 hours of reaction). The monitoring of the reaction is carried out via NMR of the proton $^1$H and/or $^{13}$C and/or $^{11}$B.
3. When the reaction is finished (which corresponds to the appearance of the signal characteristic of boron formates in $^{11}$B NMR), the solvent and the volatile compounds are evaporated under vacuum ($10^{-2}$ mbar). In certain cases, it is also possible to precipitate the boron formate by addition of pentane into the reaction medium, and the latter is then recovered via Büchner filtration.

4. The residue obtained after evaporation of the volatiles is then washed with pentane and ether in order to obtain a solid that is then dried under dynamic vacuum for at least 2 h.

Example 1: Synthesis of [Et$_3$:NH$^+$, Cy$_2$B(OCHO)$_2^-$] (R$_1$=R$_2$=Cy; X=—OCHO, Z=Et$_3$NH$^+$)

The dicyclohexylborane Cy$_2$BH is synthesised using a procedure described in the literature (A. Abiko, *Org. Synth.* 2002, 79, 103) and is then used without any particular purification.

Cy$_2$BH (481 mg, 2.7 mmol, 1 equiv.) and 5 mL of toluene are added into a 25 mL round-bottom flask provided with a magnetic bar and a J-Young valve. The suspension obtained is stirred until total dissolution of the solid and then formic acid (204 µL, 5.4 mmol, 2 equiv) is added using a syringe, followed by NEt$_3$ (377 µL, 2.7 mmol, 1 equiv) all at once. A strong release of gaseous hydrogen is observed. The reaction is then stirred for 2 h at ambient temperature and then the solvent is evaporated to dryness, leaving a very viscous oil. After multiple additions of pentane and trituration of the oil in hexane, the crystallised oil and a white solid are obtained, the latter is then recovered via filtration and washed with pentane (3×2 mL) and with ether (3×2 mL). The white solid thus recovered is dried at reduced pressure in order to obtain [Et$_3$NH$^+$, Cy$_2$B(OCHO)$_2^-$] (901 mg) with a yield of 90%.

$^1$H NMR (200 MHz, CD$_3$CN) δ 8.77 (s, 1H, NH), 8.29 (s, 2H, HC(O)O), 3.13 (t, J=7.2 Hz, 6H), 1.65 (d, J=4.3 Hz, 4H), 1.50 (d, J=12.8 Hz, 4H), 1.24 (t, J=7.3 Hz, 9H), 1.12 (d, J=7.6 Hz, 4H), 1.01-0.73 (m, 4H), 0.48 (tt, J=12.0 Hz, 2H, CH—B) ppm.

$^{13}$C NMR (50 MHz, CD$_3$CN) δ 166.43, 47.39, 29.38, 28.50, 9.06. ppm.

$^{11}$B NMR (64 MHz, CD$_3$CN) δ 11.17 ppm.

Elemental analysis: calc. (%) for C$_{20}$H$_{40}$BNO$_4$ (369.30 g·mol$^{-1}$): C, 65.04, H, 10.92, N, 3.79; found: C, 63.05, H, 11.03, N, 3.41.

Example 2: Synthesis of [Et$_3$NH$^+$, BBN(OCHO)$_2^-$] (R$_1$=R$_2$=BBN; X=—OCHO, Z=Et$_3$NH$^+$)

9-BBN dimer (1.95 g, 7.98 mmol, 0.5 equiv.) and 20 mL of toluene are added into a 100 mL round-bottom flask provided with a magnetic bar and a J-Young valve. The suspension obtained is stirred until total dissolution of the solid and then formic acid (1.2 mL, 31.92 mmol, 2 equiv) is added using a syringe, followed by triethylamine (2.2 mL, 15.96 mmol, 1 equiv) all at once. A strong release of gaseous hydrogen is observed. The reaction is then stirred for 2 h at ambient temperature then pentane (5 mL) is added then the solvent is evaporated to dryness, leaving a very viscous oil. The oil is triturated in hexane until a solid is obtained, and the white solid obtained is then recovered via filtration and washed with pentane (3×4 mL) and with ether (3×4 mL). The white solid thus recovered is dried at reduced pressure in order to obtain [Et$_3$NH$^+$, BBN(OCHO)$_2^-$] with a yield of 92%.

$^1$H NMR (200 MHz, CD$_3$CN) δ 8.60 (bs, 1H), 8.44 (s, 2H), 3.14 (q. J=7.3 Hz, 6H), 1.88-1.36 (m, 12H), 1.24 (t, J=7.3 Hz, 9H), 0.75 (bs, 2H) ppm.

$^{13}$C NMR (50 MHz, CD$_3$CN) δ 167.84, 47.46, 32.09, 25.58, 9.04 ppm.

$^{11}$B NMR (64 MHz, CD$_3$CN) δ 8.98 ppm.

Elemental analysis: calc (%) for C$_{16}$H$_{32}$BNO$_4$ (313.25 g·mol$^{-1}$): C, 61.35, H, 10.30, N, 4.47; found: C, 58.29, H, 10.13, N, 4.28.

Example 3: Synthesis of [i-Pr$_2$EtNH$^+$, BBN(OCHO)$_2^-$] (R$_1$=R$_2$=BBN; X=—OCHO, Z=i-Pr$_2$EtNH$^+$)

Via a procedure similar to that described for [Et$_3$NH$^+$, BBN(OCHO)$_2^-$] while replacing the triethylamine with diisopropylethylamine (DIPEA), the white solid [i-Pr$_2$EtNH$^+$, BBN(OCHO)$_2^-$] is obtained with a yield of 76% (766 mg).

$^1$H NMR (200 MHz, CD$_3$CN) δ 8.44 (s, 2H), 7.87 (bs, 1H), 3.68 (h, 2H), 3.15 (q, J=7.2 Hz, 2H), 1.88-1.15 (m, 27H), 0.74 (s, 2H).

$^{13}$C NMR (50 MHz, CD$_3$CN) δ 167.75, 55.47, 43.61, 32.08, 25.60, 18.57, 17.26, 12.85.

$^{11}$B NMR (64 MHz, CD$_3$CN) δ 9.03.

Elemental analysis: calc (%) for C$_{18}$H$_{36}$BNO$_4$ (341.29 g·mol$^{-1}$): C, 63.35, H, 10.63, N, 4.10. found: C, 62.80, H, 10.67, N, 3.99.

Example 4: Synthesis of [Cy$_3$PH$^+$, BBN(OCHO)$_2^-$] (R$_1$=R$_2$=BBN; X=—OCHO, Z=Cy$_3$PH$^+$)

Via a procedure similar to that described for [Et$_3$NH$^+$, BBN(OCHO)$_2^-$] while replacing the triethylamine with tricyclohexylphosphine (Cy$_3$P, 20% by weight in the toluene), the white solid [Cy$_3$PH$^+$, BBN(OCHO)$_2^-$] is obtained with a yield of 73% (729 mg).

$^1$H NMR (200 MHz, CD$_3$CN) δ 8.44 (s, 2H), 2.51 (q, J=11.7 Hz, 3H), 1.87-1.22 (m, 43H), 0.72 (s, 2H).

$^{13}$C NMR (50 MHz, CD$_3$CN) δ 166.85, 32.22, 28.88, 28.46, 28.12, 26.92, 26.66, 25.79.

$^{11}$B NMR (64 MHz, CD$_3$CN) δ 8.46

$^{31}$P NMR (81 MHz, CD$_3$CN) δ 32.21 (s).

Example 5: Synthesis of [TMPH$^+$, BBN(OCHO)$_2^-$] (R$_1$=R$_2$=BBN; X=—OCHO, Z=TMPH$^+$)

Via a procedure similar to that described for [Et$_3$NH$^+$, BBN(OCHO)$_2^-$] while replacing the triethylamine with 2,2,6,6-tetramethylpiperidine (TMP), the white solid [Cy$_3$PH$^+$, BBN(OCHO)$_2^-$] is obtained with a yield of 89% (890 mg). The white solid obtained is purified via recrystallisation in acetonitrile.

$^1$H NMR (200 MHz, CD$_3$CN) δ 8.44 (s, 2H), 7.87 (bs, 1H), 3.68 (h, 2H), 3.15 (q, J=7.2 Hz, 2H), 1.88-1.15 (m, 27H), 0.74 (s, 2H).

$^{13}$C NMR (50 MHz, CD$_3$CN) δ 169.13, 60.45, 37.22, 33.97, 29.24, 27.52, 18.51.

$^{11}$B NMR (64 MHz, CD$_3$CN) δ 8.30.

Elemental analysis: calc (%) for C$_{19}$H$_{36}$BNO$_4$ (353.31 g·mol$^{-1}$): C, 64.59. H, 10.27, N, 3.96. found: C, 64.15, H, 10.31, N, 4.02.

Base Protocol for the Reduction of Unsaturated Organic Compounds with the Boron Formates Having the Formula (I)

For the reduction of the organic compounds having an unsaturated function that can be reduced, the boron formates are reacted with the substrate to be reduced (if the latter is not the formic acid itself) or to be functionalised. The latter can be an organic compound having at least one unsaturated function that can be reduced: aldehydes, ketones, imines, carboxylic acids, amides, esters. It is also possible to add an amine (primary or secondary) in order to carry out the methylation of the latter when the substrate is the formic acid itself (dismutation conditions).

These reductions can be carried out according to the following protocol:

5. Under an inert atmosphere, in a glove box, the boron formate having the general formula (I) (0.01 to 2 molar equivalent with respect to the substrate), the substrate to be reduced, and optionally the formic acid and/or one of its derivatives, the solvent and/or the base and/or the additive are introduced into a Schlenk tube that is then sealed by a J. Young valve. The order of introduction of the reactants is not important.
6. The Schlenk is then heated to a temperature between 25 and 150° C. (preferably >80° C.) until total conversion of the formic acid (from 5 minutes to 48 hours of reaction). The monitoring of the reaction is carried out via NMR of the proton $^1$H and/or $^{13}$C and/or $^{11}$B and/or $^{31}$P.
7. When the reaction is finished (which corresponds to the disappearance of the signals characteristic of the protons of the $\underline{H}$—COO$^-$ formate in $^1$H NMR), the pressure in the tube is released. At this stage, the treatment of the reactions depends on the nature of the reduced product obtained. The examples below allow the differences in treatment of the reduction reactions according to the products obtained to be assessed.

Example 6: Formation of Methanol

According to the general protocol presented above, an NMR tube provided with a J-Young valve is filled with [Et$_3$NH$^+$, BBN(OCHO)$_2^-$] (0.125 mmol). The latter is then dissolved in acetonitrile (0.30 mL), the tube is sealed and heated at 130° C. for 19 h. The volatile compounds (MeCN and NEt$_3$) are then evaporated under vacuum (10$^{-1}$ to 10$^{-2}$ mbar), the viscous solid residue obtained is then dissolved in THF and H$_2$O (5-10 equiv. with respect to the boron formate initially introduced) is added to the reaction mixture. The solution is stirred for 30 minutes to 1 hour at ambient temperature (20±5° C.). The volatile methanol is then recovered in another Schlenk tube via transfer at a reduced pressure. An aqueous solution of methanol is thus obtained with a yield of 49%.

The table below brings together several results allowing methanol to be obtained with various boron formates and after aqueous hydrolysis (carried out as described above).

| Reactant (mmol) | Solvent | Temperature (° C.) | Time (h) | Yield (%) |
| --- | --- | --- | --- | --- |
| [Et$_3$NH$^+$,BBN(OCHO)$_2^-$] (0.125) | MeCN | 130 | 19 | 49 |
| [Et$_3$NH$^+$,Cy$_2$B(OCHO)$_2^-$] (0.125) | MeCN | 120 | 7 | 31 |
| [i-Pr$_2$EtNH$^+$,BBN(OCHO)$_2^-$] | MeCN | 130 | 7 | 50 |
| [Na$^+$,BBN(OCHO)$_2^-$] + 15-C-5 | MeCN | 130 | 24 | 58 |

Example 7: Formation of Methylated Amines

According to the general protocol presented above, an NMR tube provided with a J-Young valve is filled with [TMPH$^+$, BBN(OCHO)$_2^-$] (0.125 mmol). The latter is then dissolved in acetonitrile (0.30 mL), the tube is sealed and heated at 130° C. for 23 h. The volatile compounds are then transferred under vacuum (10$^{-1}$ to 10$^{-2}$ mbar) into another Schlenk tube. A solution consisting of TMP and of TMP-CH$_3$ (methylated TMP, 23% yield) in acetonitrile is thus obtained. The latter can be separated via distillation at a reduced pressure (T$_{eb}$ (760 mmHg or 1.0132472 bar)=152° C. and 187° C., respectively). It should be noted that the TMP regenerated at the end of the reaction can be reused in order to form [TMPH$^+$, BBN(OCHO)$_2^-$] via the method of the invention.

Example 8: Formation of Formaldehyde

According to the general protocol presented above, an NMR tube provided with a J-Young valve is filled with [Cy$_3$PH$^+$, BBN(OCHO)$_2^-$] (0.125 mmol). The latter is then dissolved in acetonitrile (0.30 mL), the tube is sealed and heated at 130° C. for 5.5 h. At this stage, the formaldehyde is obtained selectively (methanol is not observed) in the form of the acetal Cy$_3$PCH$_2$OBBN(OCHO). The volatile compounds are then transferred under vacuum (10$^{-1}$ to 10$^{-2}$ mbar) into another Schlenk tube and the solid residue obtained is then dissolved in THF and H$_2$O (5-10 equiv. with respect to the boron formate initially introduced) is added to the reaction mixture. The solution is stirred for 30 minutes to 1 hour at ambient temperature (20±5° C.). An aqueous solution of formaldehyde (28% yield) that must be used as such if needed is thus obtained.

Example 9: Reduction of Benzaldehyde into Benzyl Alcohol

According to the general protocol presented above, an NMR tube provided with a J-Young valve is filled with [EtNH$^+$, BBN(OCHO)$_2^-$] (0.10 mmol), benzaldehyde (0.05 mmol) and acetonitrile (0.30 mL), the tube is sealed and heated at 130° C. for 5 h. The volatile compounds (MeCN and NEt$_3$) are then evaporated under vacuum (10$^{-1}$ to 10$^{-2}$ mbar), the viscous solid residue obtained is then dissolved in THF and H$_2$O (5-10 equiv. with respect to the boron formate initially introduced) is added to the reaction mixture. The solution is stirred for 30 minutes to 1 hour at ambient temperature (20±5° C.). The benzyl alcohol formed is then recovered via transfer at a reduced pressure into another Schlenk tube. A solution of benzyl alcohol is thus obtained with a yield of 99%. The latter can finally be recovered and purified via distillation (T$_{eb}$ (760 mmHg or 1.0132472 bar)=203° C.).

Example 10: Reduction of Cinnamaldehyde into Cinnamic Alcohol

According to the general protocol presented above, an NMR tube provided with a J-Young valve is filled with [Et$_3$NH$^+$, BBN(OCHO)$_2^-$] (0.10 mmol), cinnamaldehyde (0.05 mmol) and acetonitrile (0.30 mL), the tube is sealed and heated at 130° C. for 5 h. The volatile compounds (MeCN and NEt$_3$) are then evaporated under vacuum (10$^{-1}$ to 10$^{-2}$ mbar), the viscous solid residue obtained is then dissolved in THF and H$_2$O (5-10 equivalents with respect to the boron formate initially introduced) is added to the reaction mixture. The solution is stirred for 30 minutes to 1 hour at ambient temperature (20±5° C.). The cinnamic alcohol formed (yield of 80%) can finally be recovered and purified via distillation (T$_{eb}$(760 mmHg or 1.0132472 bar)=250° C.).

Example 11: Reduction of 4-Chlorobenzaldehyde into 4-Chlorobenzyl Alcohol

According to the general protocol presented above, an NMR tube provided with a J-Young valve is filled with [Et$_3$NH$^+$, BBN(OCHO)$_2^-$] (0.10 mmol), 4-chlorobenzaldehyde (0.05 mmol) and acetonitrile (0.30 mL), the tube is sealed and heated at 130° C. for 5 hours. The volatile compounds (MeCN and NEt$_3$) are then evaporated under vacuum (10$^{-1}$ to 10$^{-2}$ mbar), the viscous solid residue obtained is then dissolved in THF and H$_2$O (5-10 equivalents with respect to the boron formate initially introduced) is added to the reaction mixture. The solution is stirred for 30 minutes to 1 hour at ambient temperature (20=5° C.). The alcohol 4-chlorobenzyl alcohol formed (yield of 99%) can finally be recovered and purified via distillation (T$_{eb}$(760 mmHg or 1.0132472 bar)=234° C.).

Observation:

It should be noted that the reactions leading to the methylated amines or to formaldehyde only form the latter as reduction products. In other words, the average yields observed for these reactions can be corrected by taking into account the fact that the other products are the starting products (amine of formate) or the gases CO$_2$ and H$_2$. In all cases, the latter can be reused in the method in order to prepare the formic acid or the boron formate having the formula (I).

The invention claimed is:

1. A method for reducing unsaturated organic compounds chosen from the group formed by the aldehydes, the ketones, the imines, the carboxylic acids, the amides, and the esters, wherein said unsaturated organic compound is reacted with a boron formate having the formula (I)

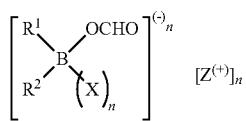

(I)

in which
R$^1$ and R$^2$, independently of one another, are chosen from the group formed by a hydroxyl group, an alkoxy group, an alkyl group, an alkenyl group, an alkynyl group, an aryl group, a heteroaryl group, a heterocyclic group, a halogen atom, a silyl group, a siloxy group, a phosphino group, and an amino group, said alkyl, alkenyl, alkynyl, alkoxy, silyl, siloxy, aryl, phosphino and amino groups being optionally substituted; or
R$^1$ and R$^2$ taken together with the boron atom to which they are bonded, form an optionally substituted heterocycle;
X is chosen from the group formed by a halogen atom, a carboxylate group, a sulfonate group, a hydroxyl group, an alkoxy group, an alkyl group, an alkenyl group, an alkynyl group, a heteroaryl group, a heterocyclic group, a silyl group,
Z is a cation chosen from the group formed by a protonated organic base having a pKa greater than 3.7 chosen from the group formed by triethylammonium (HNEt$_3^+$), di-isopropylethylammonium (i-Pr$_2$EtNH$^+$), 2,2,6,6-tetramethylpiperidinium (TMPH$^+$), and tricyclohexylphosphonium (HPCy$_3^+$); Na$^+$; Li$^+$; K$^+$; Cs$^+$; tetraphenylphosphonium (PPh$_4^+$); tetramethylammonium (NMe$_4^+$); tetraethylammonium (NEt$_4^+$); tetrabutylammonium (NBu$_4^+$) and tetraphenylammonium (NPh$_4^+$);
n is a whole number equal to 1;
in the presence of a solvent and optionally an organic or inorganic base.

2. The method according to claim 1, wherein
the aldehydes, the ketones, the carboxylic acids and the esters, are reduced into alcohols;
the imines are reduced into amines; and
the amides are reduced into amines or into alcohols.

3. The method according to claim 1, wherein in the boron formate having the formula (I),
R$^1$ and R$^2$, independently of one another, are chosen from the group formed by an alkyl group comprising 1 to 12 atoms of carbon; an aryl comprising 6 to 20 atoms of carbon, said alkyl group and aryl groups being optionally substituted.

4. The method according to claim 1, wherein in the boron formate having the formula (I),
R$^1$ and R$^2$ taken together with the atom of boron to which they are bonded, form a heterocycle comprising 5 to 10 members, said heterocycle being optionally substituted.

5. The method according to claim 1, wherein in the boron formate having the formula (I), X is chosen from the group formed a halogen atom, —OCHO and a sulfonate group having the formula —OSO$_2$R$^7$, in which R$^7$ is chosen from a methyl group (CH$_3$), a trifluoromethyl group (CF$_3$), a toluene group (p-CH$_3$C$_6$H$_4$) and a benzene group (C$_6$H$_5$).

6. The method according to claim 1, wherein Z is a cation chosen from the group formed by triethylammonium (HNEt$_3^+$), di-isopropylethylammonium (i-Pr$_2$EtNH$^+$), 2,2,6,6-tetramethylpiperidinium (TMPH$^+$), tricyclohexylphosphonium (HPCy$_3^+$), and Na$^+$.

7. The method according to claim 1, wherein the boron formates having the formula (I) are [Et$_3$NH$^+$, BCy$_2$(OCHO)$_2^-$], [i-Pr$_2$EtNH$^+$, BCy$_2$(OCHO)$_2^-$], [Et$_3$NH$^+$, n-Bu$_2$B(OCHO)$_2^-$], [Et$_3$NH$^+$, BBN(OCHO)$_2^-$], [i-Pr$_2$EtNH$^+$, BBN(OCHO)$_2^-$], [Na$^+$, BBN(OCHO)$_2^-$], [Cy$_3$PH$^+$, BBN(OCHO)$_2^-$] and [TMPH$^+$, BBN(OCHO)$_2^-$].

8. The method according to claim 1, wherein it takes place in one or a mixture of at least two solvents chosen from the group formed by:
the ethers chosen from diethyl ether, THF, diglyme, 1,4-dioxane;
the hydrocarbons chosen from benzene, or toluene;
the nitrogenous solvents chosen from pyridine, or acetonitrile;
the sulfoxides chosen from dimethyl sulfoxide;
the alkyl halides chosen from chloroform, or methylene chloride; and
a supercritical fluid chosen from supercritical CO$_2$.

9. The method according to claim 1, wherein the quantity of the unsaturated organic compounds to be reduced is from 0.5 to 2 molar equivalents, with respect to the boron formate having the formula (I).

10. The method according to claim 1, wherein it takes place in the presence of an additive chosen from:
the crown ethers chosen from the group formed by 12-crown-4, 15-crown-5, 18-crown-6, dibenzo-18-crown-6, benzo-18-crown-6, benzo-15-crown-5, and dibenzo-15-crown-5;
the aza-crowns chosen from the group formed by 1,4,7,10-tetraazacyclododecane (cyclen), 1,4,7,10,13,16-hexaazacyclooctadecane (hexacyclen), and diaza-18-crown-6;

the crown thioethers chosen from the group formed by 1,5,9,13-tetrathiacyclohexadecane (16-Ane-$S_4$), and 1,4,7,10,13,16-hexathiacyclooctadecane (18-Ane-$S_6$).

11. The method according to claim 10, wherein the quantity of additive is from 1 to 2 molar equivalents, inclusive, with respect to the boron formate having the formula (I).

12. The method according to claim 1, wherein when n=1, the boron formate has the general formula (Ib)

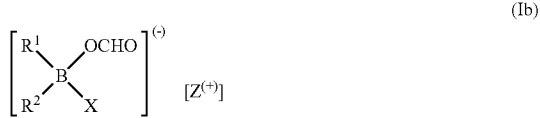

and in that the reduction takes place in the absence of a base.

13. A method for preparing methanol, comprising
(i) a step of reducing formic acid or one of its esters having the formula $HCO_2R^8$ in which $R^8$ is chosen from a hydrogen atom, an alkyl group, and an aryl group, with a boron formate having the formula (I) according to the method of claim 1,
and optionally
(ii) a step of hydrolysis.

14. A method for preparing methylated amines having the formula $R^1R^2N$—$CH_3$ with $R^1$ and $R^2$ as defined in claim 1, comprising
(i) a step of reducing formic acid in the presence of a primary amine or a secondary amine, with a boron formate having the formula (I) according to the method of claim 1, and
(ii) distillation or concentration under vacuum or column chromatography.

15. A method for preparing formaldehyde, comprising a step of reducing formic acid or one of its esters having the formula $HCO_2R^8$ in which $R^8$ in which $R^8$ is $R^8$ is chosen from a hydrogen atom, an alkyl group, and an aryl group, with a boron formate having the formula (I) according to the method of claim 1,
and optionally
(ii) a step of hydrolysis.

16. A method for preparing an alcohol having the formula $R^1CH_2OH$ with $R^1$ as defined in claim 1, comprising
(i) a step of reducing an unsaturated organic compound chosen from the group formed by the aldehydes, the carboxylic acids and the esters with a boron formate having the formula (I) according to the method of claim 1, and optionally
(ii) a step of hydrolysis.

* * * * *